United States Patent [19]

Fedor et al.

[11] Patent Number: 5,699,152
[45] Date of Patent: Dec. 16, 1997

[54] ELECTRO-OPTICAL INSPECTION SYSTEM AND METHOD

[75] Inventors: Richard L. Fedor, Mantua; Thomas H. Palombo, Akron, both of Ohio

[73] Assignee: Alltrista Corporation, Muncie, Ind.

[21] Appl. No.: 415,702

[22] Filed: Apr. 3, 1995

[51] Int. Cl.[6] .................................................. G01N 21/88
[52] U.S. Cl. .................................. 356/237; 250/223 B
[58] Field of Search ................................ 356/237, 240, 356/241, 428; 250/223 B

[56] References Cited

U.S. PATENT DOCUMENTS

| | | |
|---|---|---|
| 2,466,161 | 5/1949 | Doll et al. . |
| 2,798,605 | 7/1957 | Richards . |
| 3,107,011 | 10/1963 | Mathias et al. ............... 209/111.5 |
| 3,171,033 | 2/1965 | Mathias et al. ............... 250/224 |
| 3,857,637 | 12/1974 | Obenreder ..................... 356/120 |
| 3,886,356 | 5/1975 | Gomm et al. . |
| 3,894,806 | 7/1975 | Remy et al. . |
| 4,026,656 | 5/1977 | Kusz et al. . |
| 4,249,034 | 2/1981 | Minato . |
| 4,280,624 | 7/1981 | Ford . |
| 4,284,353 | 8/1981 | Yoshida et al. ............... 356/240 |
| 4,330,205 | 5/1982 | Murakami et al. ............ 356/237 |
| 4,376,951 | 3/1983 | Miyazawa . |
| 4,378,159 | 3/1983 | Galbraith . |
| 4,391,373 | 7/1983 | Wiggins ........................ 209/526 |
| 4,424,441 | 1/1984 | Bieringer et al. . |
| 4,428,674 | 1/1984 | Giebel et al. . |
| 4,435,641 | 3/1984 | Hajime . |
| 4,459,023 | 7/1984 | Reich et al. . |
| 4,506,980 | 3/1985 | Pryor et al. ................... 356/237 |
| 4,511,222 | 4/1985 | Biren . |
| 4,538,909 | 9/1985 | Bible et al. ................... 356/237 |
| 4,560,273 | 12/1985 | Ando et al. ................... 356/237 |
| 4,583,854 | 4/1986 | Lozar ............................ 356/237 |
| 4,606,635 | 8/1986 | Miyazawa et al. . |
| 4,626,079 | 12/1986 | Nakamuira et al. . |
| 4,650,326 | 3/1987 | Nagamine et al. ............ 356/240 |
| 4,682,023 | 7/1987 | Yoshida ......................... 250/223 B |
| 4,691,231 | 9/1987 | Fitzmorris et al. . |
| 4,758,084 | 7/1988 | Tokumi et al. ................ 356/237 |
| 4,760,270 | 7/1988 | Miller . |
| 4,865,447 | 9/1989 | Shay . |
| 4,871,257 | 10/1989 | Suzuki et al. . |
| 4,912,318 | 3/1990 | Kajiura . |
| 4,914,289 | 4/1990 | Nguyen et al. ............... 250/223 B |
| 4,924,107 | 5/1990 | Tucker .......................... 356/241 |
| 4,965,454 | 10/1990 | Yamauchi et al. ............ 250/372 |
| 5,030,823 | 7/1991 | Obdeijn ......................... 356/237 |
| 5,072,127 | 12/1991 | Cochran et al. . |
| 5,216,481 | 6/1993 | Minato . |
| 5,220,400 | 6/1993 | Anderson et al. . |

FOREIGN PATENT DOCUMENTS

| 60-98340 | 6/1985 | Japan ............................ 356/240 |
|---|---|---|

*Primary Examiner*—Richard A. Rosenberger
*Attorney, Agent, or Firm*—Brinks Hofer Gilson & Lione

[57] ABSTRACT

A system and method for inspecting opaque objects, such as metal beverage containers, is presented including a light source for illuminating the interior surface of the container, an ellipsoidal first mirror for forming a first image of an upper interior portion of the container, a first camera for capturing the first image of the upper interior portion of the container, a planar image-splitting second mirror for forming a second image of the flange of the container, a second camera for capturing the second image of the flange, an image combiner for electro-optically combining the first and second images, whereby a resultant composite image corresponding to substantially the entire upper interior surface of the container can be generated and analyzed for defects, a third camera located at a separate location for viewing directly the lower interior portion of the container and capturing a corresponding third image, and a computer means for analyzing the resulting images for defects. In an alternative embodiment, a fourth camera and a planar image-splitting third mirror may be disposed at the separate location for forming and capturing a fourth image corresponding specifically to the bottomwall of the container, and an image combiner can electro-optically combine the third and fourth images, whereby a second resultant composite image corresponding to substantially the entire lower interior portion of the container can be generated and analyzed for defects.

33 Claims, 8 Drawing Sheets

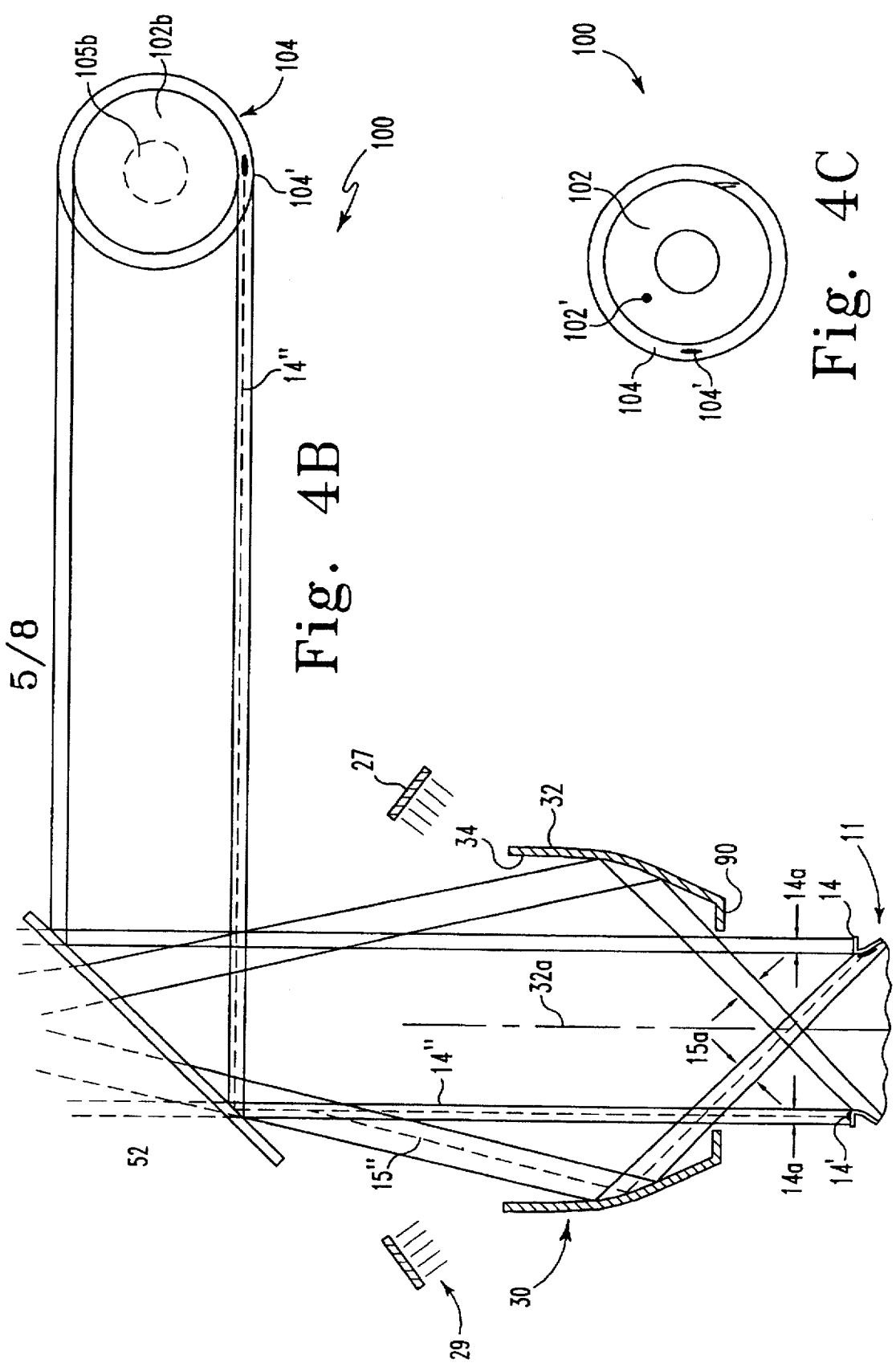

ELECTRO-OPTICAL INSPECTION SYSTEM AND METHOD

TECHNICAL FIELD OF THE INVENTION

This invention relates to means for the acquisition of images for analysis purposes, and more particularly, relates to a system and method for acquiring an image of the interior surface of an object such as a metal beverage container.

BACKGROUND OF THE INVENTION

A need presently exists in the manufacturing industry for an economical and reliable system and method for inspecting the inside surfaces of opaque objects such as metal beverage containers. Conventional manufacturing processes move aluminum beverage containers along a conveyor at line speeds of upwards to 2500–3000 containers per minute. During the manufacturing of aluminum beverage containers, for example, a number of inside surface conditions may exist which should cause the can to be rejected. The inside surfaces of such containers should be round and free of physical defects, such as dents and the like, as well as being free of grease, oil, blistered or nonuniform coatings, and debris. In addition, the flange of the container should be free of knockdowns. Such flaws or defects are sometimes produced during the manufacturing process and/or as a result of contamination after manufacture, but prior to the filling of the container.

One means by which metal containers may be inspected is a machine vision system. Machine vision is the technology of acquiring or sensing an image of a selected portion of the container through an electronic sensor and determining the existence of any marks or defects in the image and the acceptability of any such marks or defects by use of a vision computer. In machine vision technology, a television camera acquires an image and dedicated vision computers process and analyze the image. While human vision may outperform its automatic equivalent in its sheer ability to analyze very complex, every-day scenes, when it comes to repeated tasks, such as the inspection of aluminum beverage containers over and over again, a human observer understandably tires, loses concentration, and makes mistakes.

Machine vision inspection of metal containers is known to provide some important advantages, including sophisticated image processing/analysis, repeatable performance, image acquisition for diagnosis and setup, ability to inspect a variety of containers, and large tolerance in required part placement.

Automatic electro-optical inspection of glassware is well known. An example of a machine vision inspection system for detecting defects in glassware is provided by U.S. Pat. No. 4,758,084 to Tokumi, et al., which discloses an inspection apparatus having an annular illuminator, a truncated conical reflecting mirror for forming a planar image of the bottle mouth, a CCD camera for detecting the planar image and a judging unit for detecting the existence of the defects on the mouth of the bottle. The conical reflecting mirror forms a planar image of the bottle mouth by changing light rays emitted in various directions from the inner and outer surfaces of the bottle mouth into light rays parallel with each other, which are then received or captured by the camera to generate an image of the bottle mouth.

Another example is U.S. Pat. No. 4,914,289 to Nguyen et al., which discloses a system useful for the inspection of glass containers having threaded mouths. The system includes a video camera, an illumination source, a digitizer and data processor means operable to analyze a video image collected through a lens system. The lens system includes as one embodiment an elliptical mirror placed between the glass bottle and the camera for producing a distorted two-dimensional image of the bottle mouth for analysis by the data processing means.

A further example of a glassware inspection system is provided by U.S. Pat. No. 5,095,024, which is owned by the assignee of the present invention. This reference discloses a system and method for optically inspecting the bottom surfaces of transparent glass containers comprising an image acquiring means, an illumination source and means for processing, storing and analyzing the image to search for and identify a "baffle mark" in the acquired image and, when found, to remove the baffle mark from the image memory prior to the initiation of the defect inspection sequence. The baffle mark is a mold marking which is a by-product of the two-step glass manufacturing process and is generally circular in shape and may appear in different locations on the bottom of the container. It is generally an acceptable (by glass manufacturer and user) condition. In the automatic inspection of glassware by optical systems, however, the baffle mark can produce a high contrast signal which is often confused with the signal from a defect and can result in a rejection of acceptable glassware.

Yoshida, U.S. Pat. No. 4,682,023, discloses an inspection apparatus for detecting defects in the bottom and the mouth of a glass bottle. In one embodiment, the apparatus of Yoshita discloses a first photoelectric sensor arranged above the bottle for viewing and inspecting directly the bottom of the bottle and a second photoelectric sensor arranged laterally and above the bottle for receiving light reflected from a half mirror, which is positioned to intercept and redirect light rays from the bottle mouth.

Machine inspection of metal containers presents unique problems. First, the containers are inherently opaque, so the inspection system must operate on the light reflected from the metallic surfaces of the selected areas being inspected, as compared to glassware inspection systems which sense or capture light passing through the glassware.

Second, complicating the problem of inspecting the interior surfaces of a metal container is the geometry of a typical container. As shown in FIG. 1, a typical metal beverage container commonly includes a neck area 11 formed to extend upwardly and radially inwardly to define an open-topped neck of reduced radius. Such a configuration makes it very difficult to illuminate and image the interior surfaces of the container, particularly the circumferential interior surface of the neck, for inspection analysis.

Third, another problem results from the limitations in the field of vision of cameras and their effect on inspection systems and methods. With the low light levels normally reflected from the interior surfaces of a metal container, wide-lens apertures are frequently required to detect small but unacceptable defects. The depth of focus of a camera with such wide-lens apertures is narrow, and to acquire a clear and precise image, the surface portion being inspected by a single camera is consequently narrow. A typical metal beverage container, for example, has a vertical height that does not permit a single camera to generate a single focused image of the top and neck portion of a container as well as the lower interior portion of the container. Thus, it is difficult to analyze the extensive interior surface portions of a metal container.

One prior attempt at this problem involving the electro-optical inspection of metal containers is disclosed by Tucker, U.S. Pat. No. 4,924,107. Tucker discloses a system for inspecting for defects a plurality of horizontal regions on the interior surfaces of an object, such as a metal beverage container. Tucker utilizes a plurality of cameras with each camera being focused on one of the plurality of horizontal regions in the object, a lighting source for illuminating the interior of the object, means for masking out areas of interfering reflected light, and a plurality of processors for analyzing the plurality of captured images of horizontal regions. In a preferred embodiment, Tucker provides a series of three cameras physically spaced along a conveyor line. Each camera is coupled to and coacts with a separate processor, and is intended to capture an image of the inside of the beverage container at a different horizontal location for analysis of that image for defects by the separate processor. Each of the three inspection positions separately employs a camera and a processor-and-monitor combination to determine whether any defects are present in a different horizontal interior region of the container. In the event that any one of the three processors detects a defect, the system will cause the ejection of the defective container.

Another prior art attempt is disclosed by Obdeijn, U.S. Pat. No. 5,030,823, which is assigned to Heuft-Qualiplus, Netherlands. Obdeijn discloses a device for inspecting the inner surface of a hollow body, such as a metal container having a cylindrical standing sidewall and a bottom, including an annular light source for lighting the inner surfaces uniformly, a frusto-conical mirror for radiating the light rays into the container, and a video camera for inspecting the inner surfaces of the container. The light rays reflected from the interior of the sidewall of the container may be observed by the video camera via the conical mirror, or in an alternative embodiment, a curved mirror. As noted above, a predominant portion of the conventional metal beverage container made in this country today have a particular geometry that make the inspection of the interior surfaces of such containers difficult. The object of Obdeijn's system has a straight sidewall with no reduced necked portion, which is a primary cause of the imaging difficulties.

Prior art attempts aimed at inspecting the interior surface of a typical beverage container at a single inspection station have employed as many as five cameras. In such embodiments, four cameras have been equally spaced circumferentially about and above the open top of the container and a fifth camera has been located directly above the container for viewing the bottom interior portion thereof. Each of the four circumferentially arranged cameras is disposed to view downwardly and radially inwardly to inspect a different quadrant of the flange and the circumferential interior surface of the neck portion of the container. In the event any one of the five cameras detects a defect, the container is rejected. Such prior art systems are, understandably, large, complex, expensive and difficult to program.

Thus, major shortcomings in the application of conventional machine vision systems for the inspection of interior surfaces of opaque objects, especially the interior surfaces of typical metal beverage containers, include their expense, complexity, operating difficulty and size. A need, therefore, presently exists for a more compact, less complex and less expensive system for inspecting reliably, at high speeds, the interior surfaces of a metal container to detect the presence of unacceptable defects.

SUMMARY OF THE INVENTION

This invention presents a system and method for inspecting the top and interior portions of conventionally manufactured metal beverage containers for use on a conveyor line transporting a plurality of such containers during their manufacture. This invention permits inspection of metal beverage containers and the identification of defects present therein at the high manufacturing speeds commonly used today with a high degree of reliability.

More particularly, this invention provides a system for use on a conveyor line for inspecting the interior surfaces of such containers and includes, at a first inspection station, an illuminator for illuminating at least an upper interior portion of the container, a first means located generally above the Container for forming a first image of the upper interior portion of the container, a second means for sensing the first image thus formed, a third means located above the top of the container for forming a second image of the flange of the container, a fourth means for sensing the second image thus formed and, preferably, a fifth means coupled to the image-sensing means for combining the first and second images to generate a resultant composite image of the entire upper portion of the container for defect analysis and processing. This invention further includes, at a separate inspection station, a sixth means located above the container for sensing directly a third image of the lower interior portion of the container and a seventh means coupled to the image-sensing seventh means for analyzing the third image for defects.

In a further embodiment of this invention, the system can include, at the separate inspection station, an eighth means located above the top of the container for forming a fourth image of the bottomwall of the container and a ninth means for sensing the fourth image, which is also coupled to the image-analyzing seventh means. In this further embodiment, the image-analyzing seventh means, located at the separate inspection station, is further adapted to combine the third and fourth images to generate, for defect analysis and processing, a second resultant composite image of the entire lower interior portion of the container generally below the neck area.

The illuminating means of this invention preferably comprises an annular illuminator disposed generally above and around the open top of the container to direct light at the upper interior portion of the container. The image-forming first means of this invention preferably comprises an annular reflecting member adapted to form an image of the upper interior portion of the container within the operating field of the image-sensing second means. A preferred annular reflecting member has an ellipsoidal cross-section that provides the image-sensing second means with additional perspectives not practical or possible with conventional lensing, as well as with the ability to form an enlarged two-dimensional image of the three-dimensional circumferential surface of the upper interior portion of the neck of the container. The image-forming third and eighth means of this invention each preferably comprise a planar image splitting mirror arranged above the container for permitting the image-sensing sixth and ninth means, respectively, to view and capture the respective images of the container. The image-sensing second, fourth, sixth and ninth means of this invention each preferably comprise a television camera. The image-processing means of this invention are preferably defined by vision computers that can be coupled to the television cameras for receiving and processing the respective images sensed by the cameras.

In addition, the invention can be provided with user interface means coupled to the system to allow an operator to communicate with the system. The system can also provide for the removal or rejection of unacceptable containers from the conveyor line.

As noted above, the system of this invention is specifically intended to be used in the inspection of metal beverage containers having neck portions of reduced radii. Such containers commonly include an upper neck portion, which includes the top flange circumscribing the open end of the container and the circumferential portion of the neck portion, and a lower interior portion, which includes the cylindrical sidewall generally below the neck portion and the bottomwall of the container. In such preferred systems, the illuminator is arranged at the first inspection station to illuminate at least the circumferential area of the upper interior portion of the neck of the container. The image-forming first means, preferably defined by the ellipsoidal annular reflecting member disposed generally above and coaxially with the container, intercepts light rays reflected from the circumferential area of the upper interior portion of the neck and forms an enlarged corresponding first image, which is then captured by the image-sensing second means defined by one of the pair of television cameras located at the first inspection station. The ellipsoidal annular reflecting member is, in a sense, thus capable of "unfolding" this very difficult area of the interior surface of the container neck by intercepting the lights rays reflected therefrom and redirecting them to be captured by the image-sensing second means. The image-forming third means located at the first inspection station is preferably angularly disposed between the container and the image-sensing first means and intercepts light rays reflected from the flange of the container and forms a corresponding second image, which is then captured by the image-sensing fourth means. The image-sensing second and fourth means direct their respective images to the fifth means (vision computer), which combines the first and second images and generates for defect analysis a single, high-resolution composite image of the entire upper portion of the container.

At the second inspection station provided by this invention, the image-sensing sixth means, preferably defined by a third television camera, is positioned generally above and coaxially with the container such that it can observe directly the lower interior portion of the container and capture a third image corresponding thereto. The image-sensing sixth means can then direct the third image to be analyzed for defects.

In the alternative embodiment, the image-forming eighth means, defined by a second planar image-splitting mirror angularly disposed between the image-sensing sixth means and the container, intercepts light rays reflected from the bottom wall of the container and forms a corresponding fourth image, which is then captured by the image-sensing ninth means preferably defined by a fourth television camera. The image-sensing sixth and ninth means can then direct their respective images to the image-processing seventh means, which is preferably defined by a second vision computer that combines the third and fourth images and generates for defect analysis a second single, high-resolution composite image of the entire lower interior portion of the container.

A method provided by this invention for acquiring images of the interior surfaces of an opaque object such as a metal beverage container generally includes the steps of illuminating the interior of the container, forming a first image of one interior surface portion adjacent the top of the container, capturing the first image thus formed, forming a second image of a second surface portion adjacent the upper portion of the object, capturing the second image thus formed, combining the first and second images to thereby form a resultant third composite image of the upper portion of the object, and capturing a third image of the interior surface of a lower portion of the object. The method of this invention can additionally include the step of analyzing and processing the captured images for defects.

The method of this invention more particularly includes acquiring images of substantially the entire interior surface of an open top metal beverage container, comprising the steps of: illuminating the open top of the container; forming an image of the circumferential interior area of the upper portion of the neck of the container with the annular reflector; forming a second image of the flange of the container by directing light reflected therefrom toward the second camera with the planar image-splitting mirror; capturing the light reflected from the circumferential interior surface of the neck with the first camera; capturing the light reflected from the flange with the second camera; combining the images of the upper interior portion and the flange of the container for defect analysis; determining whether a defect exists in the resultant combined image; capturing a third image of the lower interior portion of the container with a third camera arranged at a separate location; and analyzing the third image for defects. The method of this invention can additionally include, at the separate inspection station, the steps of: forming a fourth image of the bottom wall of the container by directing light reflected therefrom toward a fourth camera with the second image-splitting mirror; capturing the light reflected from the bottom wall with the fourth camera; and combining the third and fourth images for defect analysis. Such a method can be used advantageously for inspection of metal beverage containers.

Further features of the invention will be apparent from the following drawings and the disclosure of a preferred embodiment of the invention and its method of operation.

BRIEF DESCRIPTION OF THE DRAWINGS

FIG. 4B is a partial cross-section of the inspection station of FIGS. 2 and 3, illustrating the manner in which the planar reflector of this invention forms an image of the flange of the container;

FIG. 4C illustrates the resultant combined image formed by the working arrangement of FIGS. 2–4;

BEST MODE FOR CARRYING OUT THE INVENTION

Figure 1:
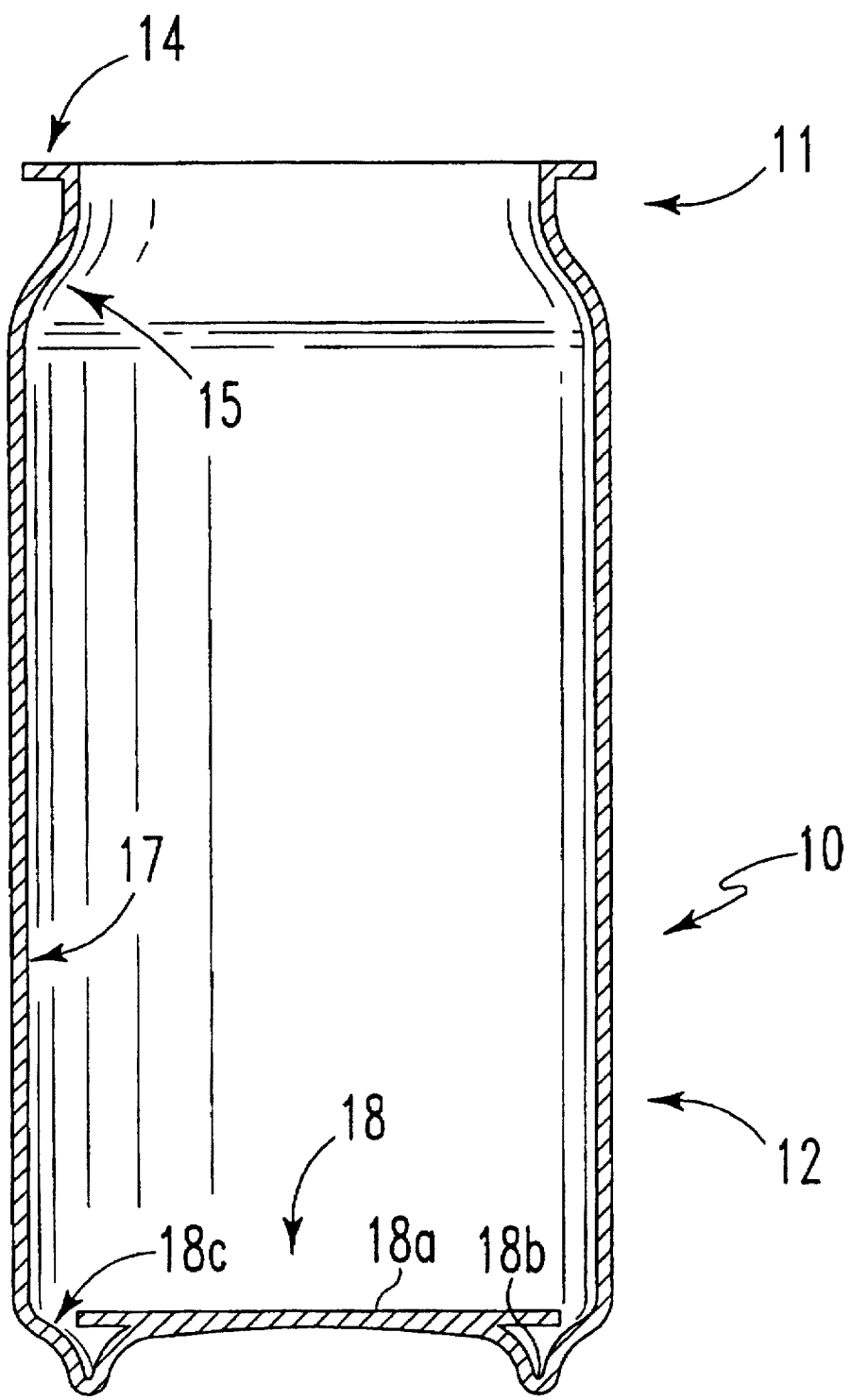
FIG. 1 is a profile of a typical metal beverage container.

This invention generally presents a system and method for inspecting the interior surfaces of an opaque object, such as a typically formed metal beverage container 10 as shown in FIG. 1. Such a metal beverage container 10 commonly includes an upper portion 11 and a lower portion 12 defined by a cylindrical sidewall 17 and a bottomwall 18 including a crown 18a, a moat 18b and a chime 18c. Upper portion 11 includes a top surface defined by flange 14 circumscribing the open top of the container and a neck portion 15 of reduced diameter relative to the cylindrical sidewall 17 of the container. For quality control considerations, the flange 14 must be round and free of knock-downs and the interior surface of the neck 15 must be free of any surface imperfections and any grease residue remaining from the neck forming operation.

This invention uses a two-stage inspection process utilizing a combination of cameras and reflecting members, and a vision computer to inspect substantially the entire interior surface of container 10 by acquiring and analyzing an image of the upper portion 11 at one inspection station and by acquiring and analyzing an image of the lower portion 12 at a separate inspection station. If the system of this invention detects a defect in any image so acquired, it can effect the removal of the defective container. The following types of defects may be detected by this invention: knocked-down flanges, dents, internal lithography, necker grease, out-of-round portions and nonuniform coatings.

Figure 2:
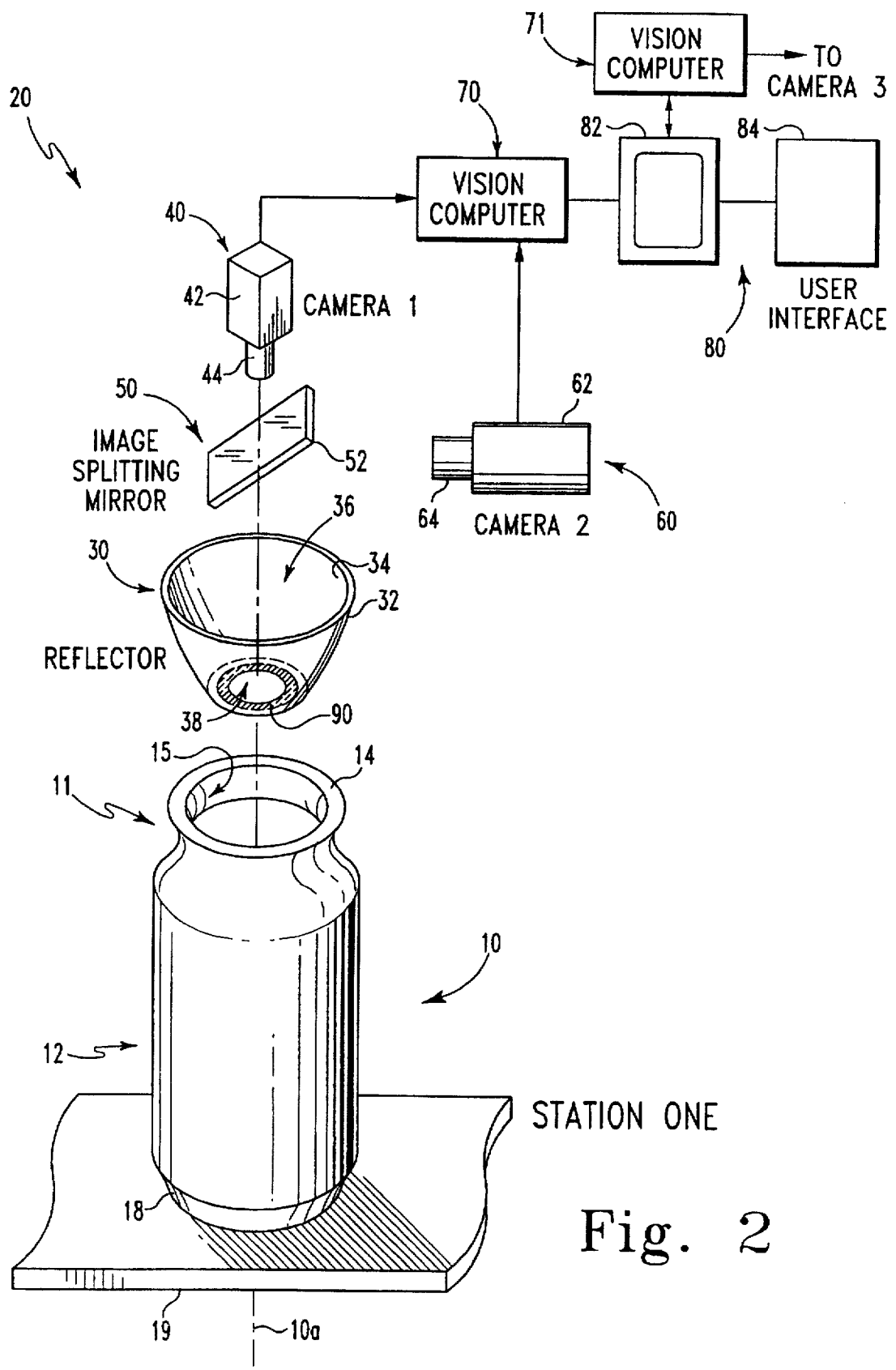
FIG. 2 is a perspective view of a single station system provided by the inspection system of this invention.
Figure 3:
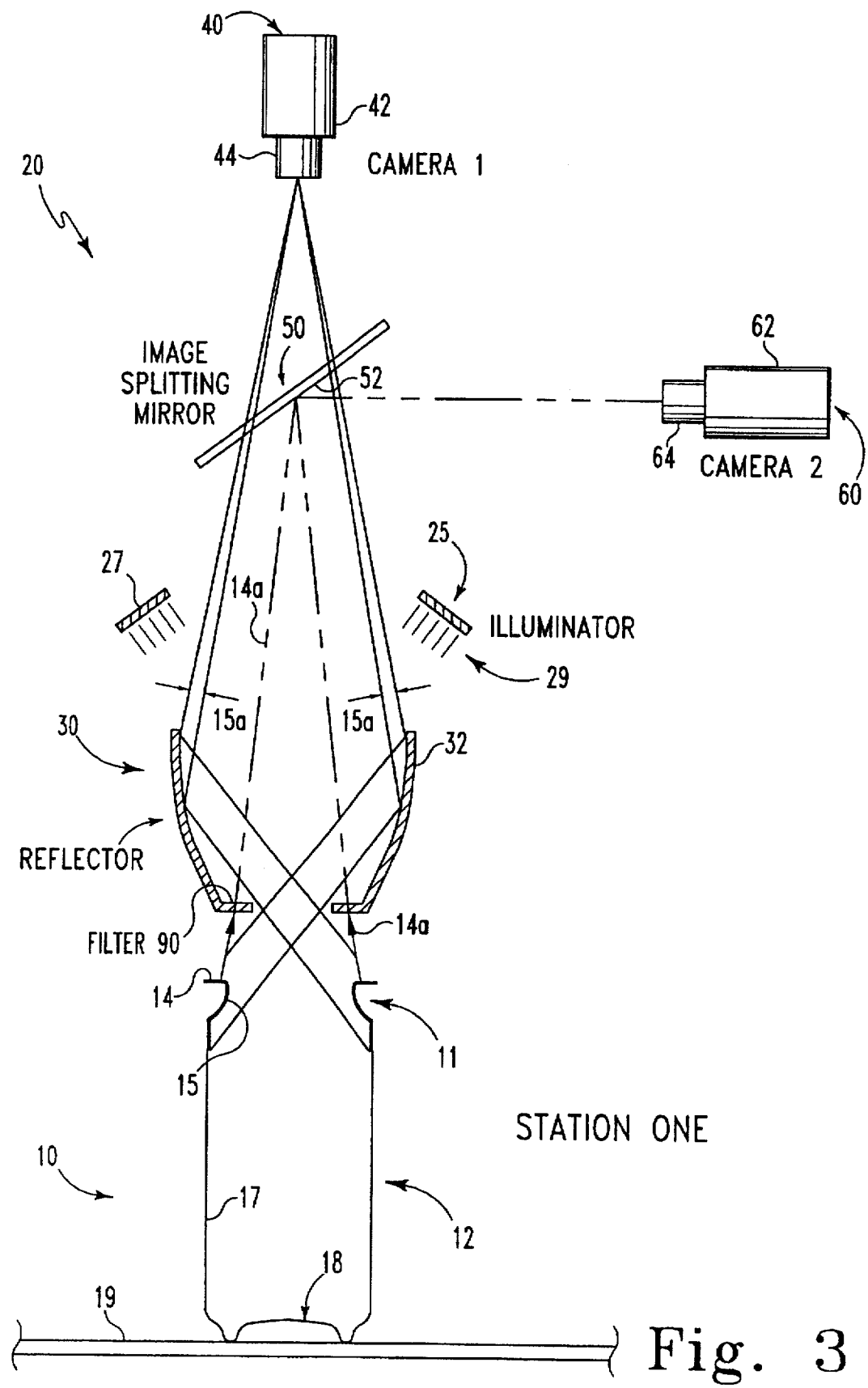
FIG. 3 is a schematic elevation and partial cross-sectional view of the working arrangement of the inspection station of FIG. 2 for acquiring a composite image of the upper portion of a container.

As shown in FIGS. 2 and 3, this invention preferably comprises a system 20 located at a first inspection (Station One), including means 25 (not shown in FIG. 2) for illuminating at least the interior of the upper portion 11 of container 10 including the interior circumference of neck 15, image-forming first means 30 located above the container 10 for forming a first image of the circumferential interior portion of neck 15, an image-reproducing second means 40 for capturing and reproducing the first image thus formed, an image-forming third means 50 located above the top of the container 10 for forming a second image of the flange 14 of container 10, an image-reproducing fourth means 60 for capturing the second image thus formed, and, preferably, an image-processing means 70 coupled to the image-sensing second and fourth means 40 and 60 for electronically combining the first and second images and generating a resultant composite image of the upper portion 11 of container 10 for defect analysis.

System 20 of this invention can further include operator interface means 80 coupled to system 20 for allowing an operator to communicate with the system 20. Even further, this invention can include machine interface means (not shown) for allowing this invention to communicate with remote machines, such as a rejection machine, to effect the removal of defective containers from the conveyor line 19.

Image-forming first means 30 preferably comprises an annular reflector 32 having an inwardly facing reflecting surface 34, an upper opening 36 and a lower opening 38, which is smaller than upper opening 36 because of the shape of reflector 32. To provide for the effective enlargement of the first image of the circumferential interior surface of the neck 15 of upper portion 11, annular reflector 32 is formed with a curved cross-section. As shown in FIGS. 2 and 3, annular reflector 32 has the shape of a truncated, three-dimensional ellipsoidal or upwardly concave parabolic member. Annular reflector 32 is well adapted to form, above the top of the container, an enlarged image of the upper interior portion 15, allowing image-reproducing second means 40 to thereby inspect upper interior portion 15 with an enlarged angle of aperture. Thus, the preferred ellipsoidal annular reflector 32 is specifically adapted to "unfold" the image of the upper interior portion 15 by intercepting light rays reflected from the interior surface thereof and redirecting the intercepted light rays to form an enlarged image thereof, which image can then be captured by image-sensing means 40.

The image-forming third means 50 of this invention preferably comprises a planar image-splitting half mirror or reflector 52 arranged above the container 10 between the container and image-sensing means 40 for permitting the image-reproducing fourth means 60 to sense or capture an image of the flange 14 of container 10. Planar reflector 52 generally lies along a central axis 10a of container 10 in a plane disposed at an angle of approximately 45 degrees in relation to central axis 10a. Image-sensing means 60 is correlatively located with its optical or central axis arranged approximately 90 degrees in relation to central axis 10a. While preferred angles have been disclosed, other angles of orientation of mirror 52 and image-sensing means 60 may be utilized.

The image-sensing second and fourth means 40 and 60 employed by system 20 each preferably comprise a television camera 42 and 62, respectively, with each said camera being equipped with a lens 44 and 64, respectively. Lens 44 of camera 42 is specifically provided with the proper aperture and depth of focus to encompass and capture the enlarged image of the upper interior portion 15 of container 10 formed by the annular reflector 32. For example, camera 42 can be operated with a lens having an f-stop of aperture with a focal length of 25 to 50 mm, permitting the first system 20 to capture a two-dimensional image of the three-dimensional upper interior portion 15 with the camera having a sensitivity as low as 5 Lux. Lens 64 of camera 62 is specifically provided with the proper aperture and depth of focus to encompass and capture the image of the flange 14 formed by the planar reflector 52.

Illumination means 25 provided by this invention at Station One (FIG. 3) preferably comprises an annular array 27 of light-emitting diodes disposed in a front-lighting arrangement in relation to container 10. Annular array 27 is preferably located above the open top of container 10 and between the image-forming first means 30 and the camera 42 and is adapted to direct light rays 29 generally downwardly and radially inwardly to illuminate particularly the circumferential interior surface 15 of upper portion 11. Such an arrangement causes light rays to illuminate the flange 14 and the circumferential interior surface portion 15.

Camera 42, annular diode array 27 and annular reflector 32 are preferably arranged generally coaxially, that is, so that their central axes generally coincide with each other, and with central axis 10a of container 10.

As shown in FIG. 2, image processing means 70, defined by a vision computer, and user interface means 80 are preferably coupled to cameras 42 and 62 to receive their respective images and to provide for the programming of system 20 by the use of a monitor 82, menus presented thereon, and a keyboard 84. As noted above, vision computer 70 is adapted to combine the first and second images sensed and reproduced by cameras 42 and 62, respectively, and generate a resultant composite image and substantially contemporaneously inspect the resultant composite image for defects.

The flange 14 of upper portion 11 presents a highly reflective flat surface which, when illuminated, presents a problem in conventional machine vision inspection systems. As noted above, the upper interior portion of a typical metal beverage container is very difficult to illuminate and image for inspection purposes because of the geometrical shape of the upper portion. Typically, when an illumination means projects light of sufficient intensity to properly illuminate the interior of the container for imaging, it results in a high intensity light being reflected off flange 14, which often interferes with a machine vision system's ability to acquire images of selected interior portions of the container. This phenomenon is commonly referred to as "washing out". To solve this problem, lens 64 of camera 62 is specifically provided with the proper aperture to control the intensity of the light reflected from the flange 14 to prevent "wash-out." Furthermore, because material handling systems are seldom able to position the container to be inspected precisely in the desired location, there is frequently a slight deviation between the central axis 10a of the container and the central and optical axis(es) of the inspection system. Lens 64 must therefore have sufficient field of view to accommodate such deviations and control the high intensity reflected light rays 14a from flange 14. Preferably, part-present sensors are employed to strobe illuminator 27 and initiate the inspection sequence when the container is positioned very near the center of system 20, as is well known in the art.

In some systems, the high intensity light from the flange can be controlled or further controlled by filtering means defined by an annular optical filter 90 (shown in dashed lines in FIG. 2) for filtering the light rays 14a reflected from flange 14 and reducing their intensity before the light rays are received by the cameras. Filter 90 is preferably positioned adjacent the lower opening 38 of annular reflector 32 above the container 10. Where used, annular filter 90 is preferably provided with sufficient inner and outer diameters to accommodate deviations in the relative positioning between the container 10 and the system 20, while still reducing the intensity of the light rays 14a and permitting lights rays 15a reflected from the upper interior portion 15 to pass through its central opening to be intercepted by annular reflector 32 and redirected to first camera 42.

The operation of the first system 20 of this invention will now be described in more detail with specific reference to FIGS. 3, 4A and 4B.

Referring now particularly to FIG. 3, with a container 10 in position, annular diode array 27 is operative to irradiate at least the interior portion 15 of upper portion 11 with diffused light rays 29. Light rays 15a reflected from the upper interior portion 15 are then intercepted by annular reflector 32, which forms a first image corresponding to upper interior portion 15 and redirects the light rays 15a toward camera 42 to be captured thereby. The first image thus captured is then directed by first camera 42 to vision computer 70. Planar image-splitting reflecting member 52, which is angularly disposed between the annular reflector 32 and the first camera 42, intercepts light rays (indicated by double-dashed reference lines 14a) reflected from the flange 14 of the container 10 and forms a corresponding image, which is then captured by second camera 62. Second camera 62 then directs the second image thus captured to vision computer 70 (FIG. 2).

Figure 4A:
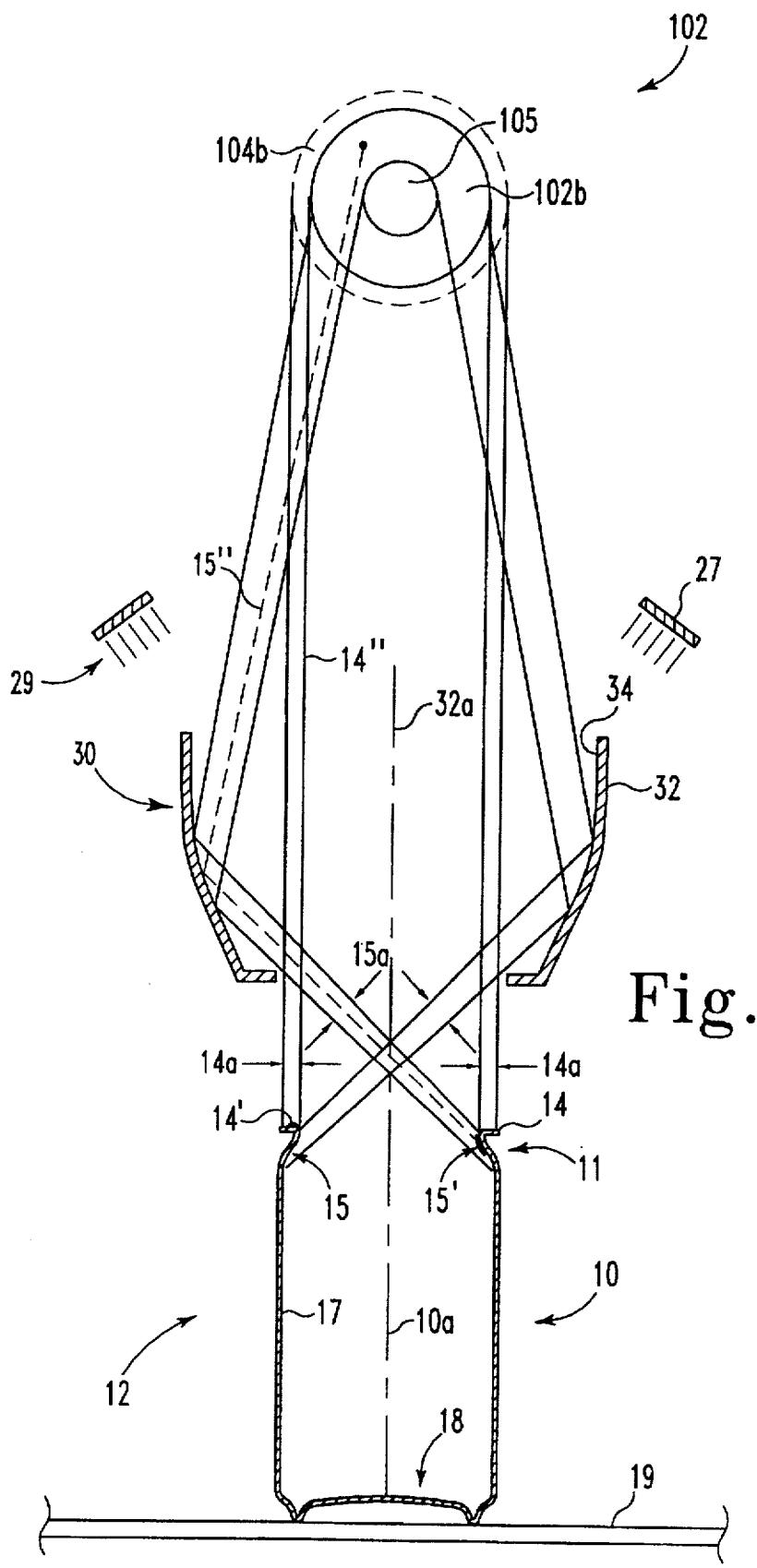
FIG. 4A is a partial cross-section of the inspection station of FIGS. 2 and 3, illustrating the manner in which an annular reflector of this invention forms a first image of the upper interior portion of the necked area of a metal container.

FIGS. 4A and 4B collectively present a schematic elevation, partly in cross-section, of the manner in which a composite image 100 of the upper portion 11, including flange 14 and the interior of neck portion 15, is formed and captured by the system 20 of this invention. (Image 100 is turned 90 degrees into the plane of the paper for purposes of illustration in FIGS. 4A and 4B and the means for acquiring an image of the flange 14, i.e., image-splitting mirror 52 and second camera 62, are omitted from FIG. 4A for purposes of clarity.) As shown in FIGS. 4A and 4B, the central axes 10a and 32a of container 10 and annular reflector 32, respectively, coincide with each other so that light rays 15a reflected from the upper interior portion 15 of the neck 11 are directed generally upwardly and are captured by camera 42 via annular reflector 32 to form a first image 102, which is then directed to the vision computer 70. Light rays 14a reflected from flange 14 are likewise directed generally upwardly to form an image portion 104b. Vision computer 70 is adapted to mask out all of the portion of the image portion 104b and the image portion 105 corresponding to the sidewall 17 and bottomwall 18, which is generally out of focus in any event and thus contains no useful information subject to accurate analysis by the system.

As shown in FIG. 4B, the image 104 of flange 14 is formed by the half-silvered planar reflector 52 for capture by camera 62, as shown in FIG. 3. FIG. 4B omits the bottom portion of container 11 and cameras 42 and 62 to simplify the illustration of the invention. The image portions 102b and 105b correspond to the interior portion of flange 15 and the sidewall 17 and bottomwall 18. The image formed on reflector 52 and captured by camera 62 is directed to vision computer 70, which is adapted to mask out image portions 102b and 105b and thereafter combine the first and second video images 102 and 104 to generate resultant composite image 100 as shown in FIG. 4C, wherein the first image 102 corresponding to upper interior portion 15 is placed concentrically inside the second image 104 of flange 14. Composite image 100 is then sent on to be processed by vision computer 70.

In this process, light from the underside of the upper interior portion 15 is reflected by the annular reflector 32 upwardly to for image 102. In this manner, the image of the circumferential interior surface of the neck 11 has been "unfolded" and appears two-dimensional to the first camera 42.

In the event a defect 15' exists on the upper interior portion 15 of the neck 11 (FIG. 4A), a corresponding defect image 102' appears in image 102 via annular reflector 32 (FIGS. 4A and 4C). Similarly, in the event a defect 14' exists on flange 14, a corresponding defect image 104' appears in the second image 104 via planar reflector 52 (FIGS. 4B and 4C). Defect images 102' and 104' are formed from light rays that are reflected irregularly from the defects 15' and 14', respectively, resulting in a light contrast in image 100 which can be detected optically by vision computer 70. For purposes of illustration, the light contrasts which produce the defect images 102' and 104' are indicated by dashed reference lines 15" and 14", respectively. The system 20 of this invention may include, if desirable, further masking means (electronic or mechanical) to block out any portions of the images captured by the cameras corresponding to particular interior portions of container 10.

Thus, as described above, first system 20 of this invention located at a first inspection station acquires a resultant composite first image 100 of, preferably, the flange 14 and the upper interior portion 15 of neck 11, and electronically combines the first and second images via vision computer 70 to generate the resultant composite image 100, shown in FIG. 4C, which is then analyzed and processed for any defects existing in the corresponding portions of the container. Composite image 100 includes annular image 104 corresponding to flange 14 as acquired by, preferably, second camera 62 via planar reflector 52, and annular image 102 corresponding to the upper interior portion 15 of neck 11 as acquired by, preferably, first camera 42 via annular reflector 32. It is not necessary in the effective operation of this invention that first camera 42 necessarily captures the first image 102 of the upper interior portion 15 while the second camera 62 captures the second image 104 of the flange 14 of container 10. System 20 may be alternatively configured so that first camera 42 captures the image of the flange 14 while second camera 62 captures the image of the upper interior portion 15.

Figure 5:
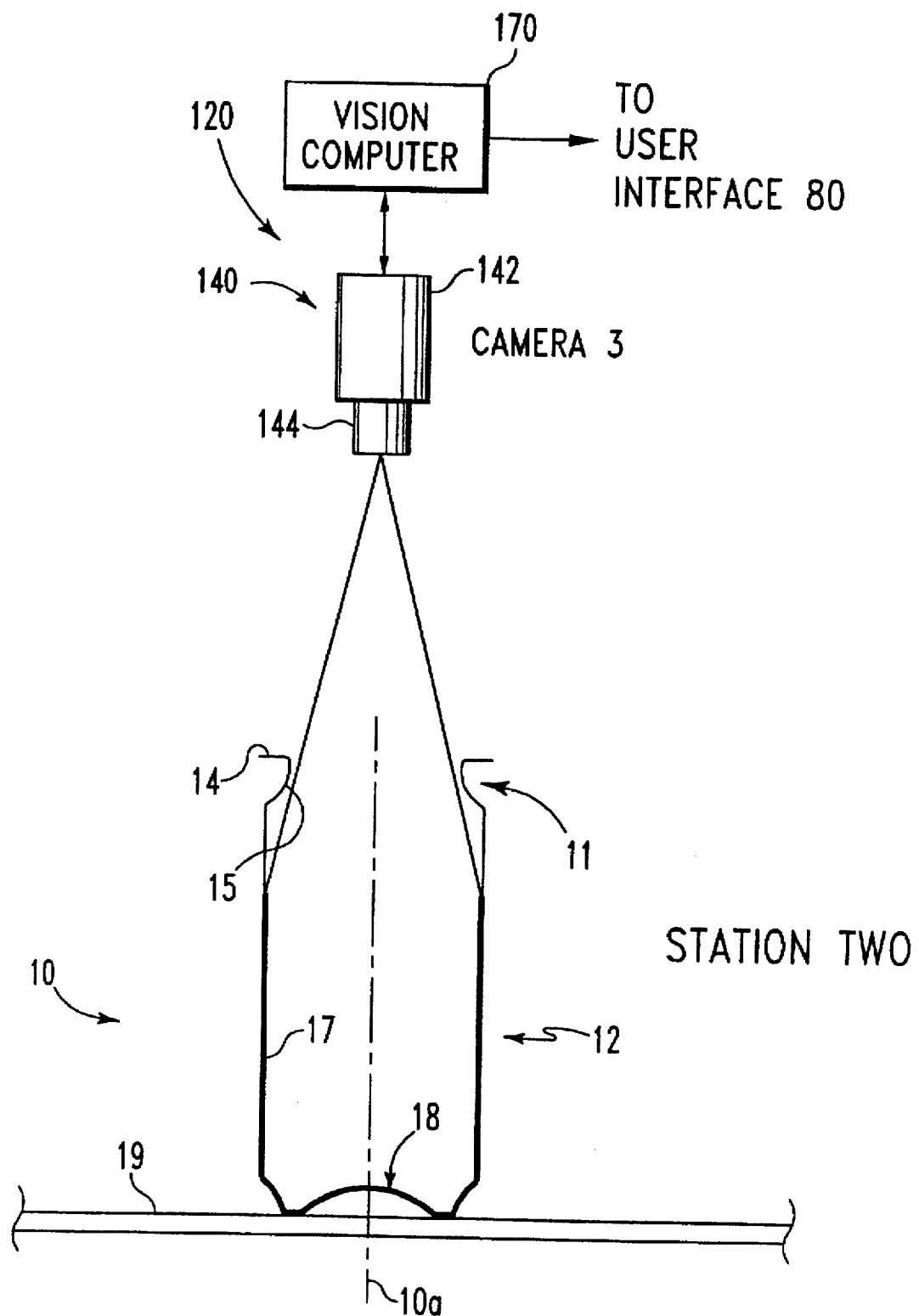
FIG. 5 is a schematic elevation and partial cross-sectional view of the working arrangement of a second system of this invention located at a separate inspection station for acquiring an image of the lower interior portion of a container.

Referring now to FIG. 5, this invention can additionally include a second system 120 arranged at a separate inspection station (Station Two) for acquiring an image of the interior surfaces of the lower portion 12 of container 10 generally below necked portion 15. In a preferred embodiment of this invention, second system 120 comprises an image-sensing sixth means 140, defined by a third television camera 142 equipped with a lens 144, and a second image analyzing means defined by a second vision computer 170 coupled to camera 142. Vision computer 170 is preferably also coupled to user interface 80 as shown in FIG. 2. Camera 142 is preferably arranged such that its central optical axis coincides with central axis 10a of container 10. Lens 144 of camera 142 is specifically provided with the proper aperture and depth of focus to view the interior surface of lower portion 12 (indicated by a heavier shaded line) and capture a two-dimensional third image corresponding thereto, which image is then directed by camera 142 to vision computer 170 for defect analysis. The third image so acquired by system 120 includes respective portions corresponding to the sidewall 17 and bottomwall 18 of container 10.

Figure 6:
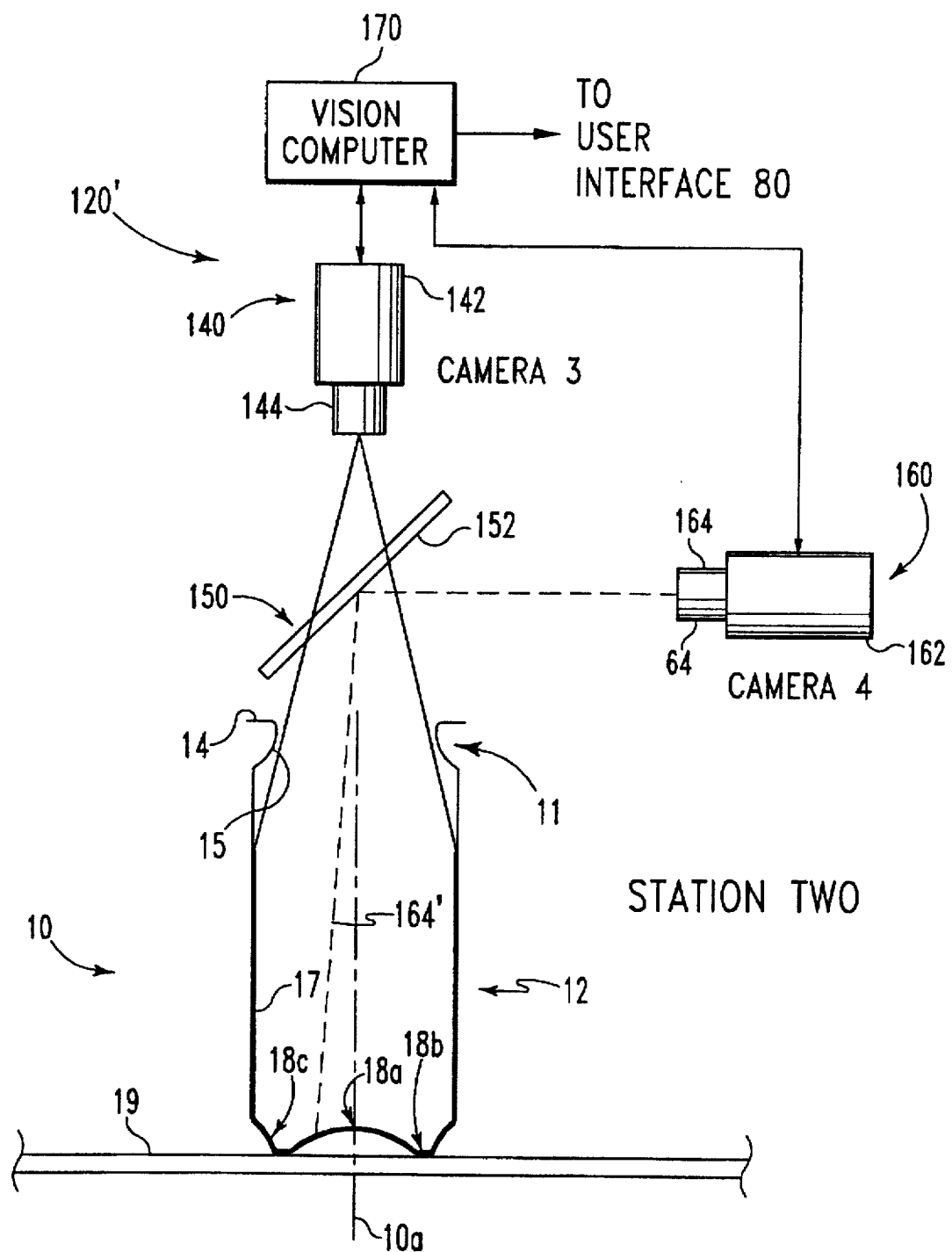
FIG. 6 is a schematic elevation and partial cross-sectional view of an alternative embodiment of the second system of FIG. 6 as provided by this invention.

In an alternative embodiment of this invention, the separate inspection system, referenced as 120' in FIG. 6, can additionally include an image-forming eighth means 150 located generally between the container 10 and the third camera 142 and image-reproducing ninth means 160. In this alternative embodiment, image-forming eighth means 150 comprises a planar image-splitting mirror 152, which is substantially identical to mirror 52 of first system 20, and which lies along central axis 10a in a plane disposed at an angle of approximately 45 degrees in relation to central axis 10a. Image-reproducing ninth means 160, defined by a fourth television camera 162 equipped with a lens 164, is correlatively located with its optical or central axis arranged approximately 90 degrees in relation to central axis 10a. (Again, other angles of orientation of mirror 152 and camera 162 may be utilized.) Planar mirror 152 is adapted to form a fourth image of the bottomwall 18 of container 10, including crown 18a, moat 18b and chime 18c, and fourth camera 162 is adapted to sense or capture the fourth image thus formed. Lens 164 of camera 162 is specifically provided with the proper aperture and focus depth (generally indicated by reference line 164') to encompass and capture the fourth image corresponding to bottomwall 18 via planar mirror 152. Camera 162 is adapted to direct the fourth image once captured to vision computer 170 for analysis.

Figure 7:
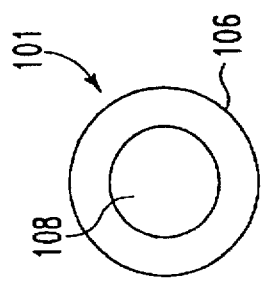
FIG. 7 shows a schematic view of the resultant video image of the interior surfaces of the lower portion of the container as acquired and generated by the inspection station of this invention shown in FIG. 6.

In this alternative embodiment, vision computer 170 can include means for masking the third image to mask out that portion of the third image corresponding to bottomwall 18 to thereby modify the third image to include only an image segment corresponding generally to the sidewall 17 of container 10, and for thereafter combining the third image so modified with the fourth image from camera 162 to generate a second resultant composite image 101 as shown in FIG. 7. Image 101 includes the third image referenced 106 corresponding to the cylindrical sidewall 17 of container 10 and the fourth image referenced 108 corresponding to the bottomwall 18, including crown 18a, moat 18b and chime 18c.

Once second resultant composite image 101 is generated by system 120', it can be inspected for defects by vision computer 170. While the present invention contemplates employing a separate vision computer at each of the two inspection stations, a single vision computer can be coupled to all of the cameras for receiving and processing their respective images.

Figure 8:
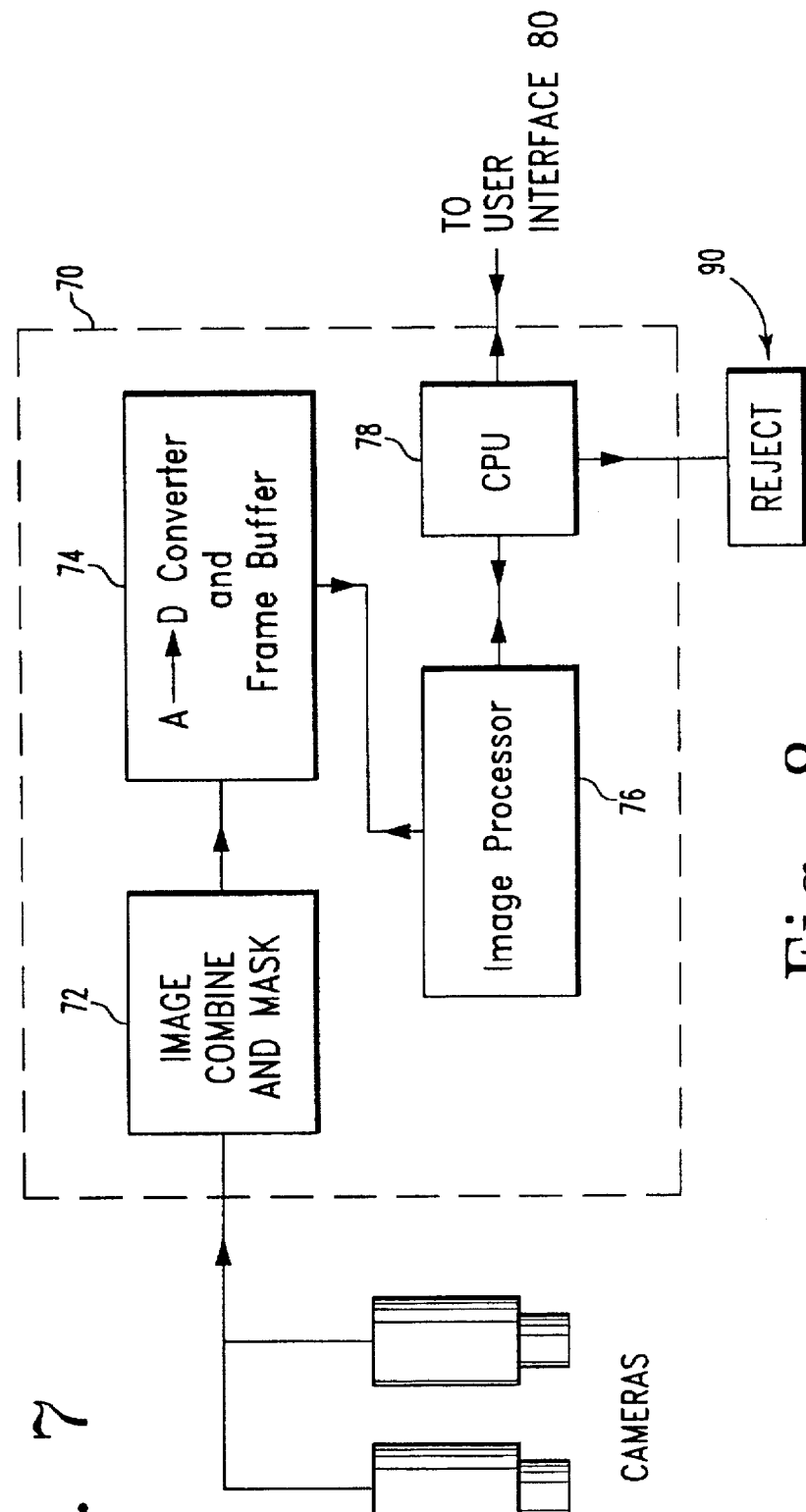
FIG. 8 is a block diagram of a typical vision computer system utilized in the inspection system of this invention.

The cameras employed by this invention are adapted to capture and store their respective images for a brief moment (milliseconds) in a memory matrix array, which comprises a plurality of separate memory locations, each of which represents a single picture element ("pixel"). The cameras act as a source of image signals that can be directed to the vision computer(s) employed by this invention. As shown in FIG. 8, when an image is captured by a camera and directed to the vision computer, the image is initially received by an image-combining and -masking means 72 on the next vertical blanking signal. Means 72 is adapted to mask the corresponding image signals as described above and combine them accordingly, if necessary, to generate resultant composite images 100 and 101. Means 72 may comprise a separate electronic component or may be integrally combined as part of a vision computer 70 or 170. The vision computer can be operated to identify unacceptable marks (such as defects images 102' and 104' in FIG. 4C) present in the resultant composite images 100 and 101 and cause the removal of an unacceptable container from the conveyor line 19.

The vision computer utilized by this invention is preferably based upon a multi-processor system design comprising an image combining and masking means 72, an analog-to-digital converter and frame buffer means 74, an image processor 76, and a CPU 78. As noted above, vision computers 70 and 170 are substantially identical, except an image-masking and -combining means 72 may be omitted from second vision computer 170 in the preferred embodiment of second system 120 shown in FIG. 5. Means 72 is adapted to receive the respective images from the cameras, electronically mask out those portions of the images out of focus or that contain no desired information, and combine the images to generate resultant composite image for subsequent defect analysis. Means 74 is adapted to digitize the analog signals received from the cameras, and then store the resultant digitized signals. After the digitized resultant composite image has been stored in means 74, the image is then ready to be analyzed by the image processor 76. The instructions for these processing operations may be provided by a PROM or CPU 78 or may be communicated through the user interface 80. Image processor 76 executes these instructions using predetermined parameters retrieved from a CPU RAM. The results of the inspection job may then be directed into a mailbox memory means for subsequent use by the CPU 78.

As noted above and as shown in FIG. 2, user interface 80 allows an operator to communicate with the systems 20 and 120 of this invention and generally includes the monitor 82, keyboard 84 and can include an LED remote I/O display (not shown). The monitor 82 displays the video images of the interior portions of the container 10 being inspected, as well as various prompts and instructions directed to the operator. This invention can additionally include machine interface means (not shown) for allowing the systems to communicate with remote rejection machines. Such rejection machines can be provided by various conventional pneumatically actuated rejection devices.

A suitable vision computer for use with this invention may be provided by the processing unit commercially available from Alltrista Corporation, LumenX Company, Mogadore, Ohio, as a product trademarked as FAST TRACK. The FAST TRACK machine vision processing unit converts the image sensed by the cameras into binary images by applying an edge detection algorithm. An example of the operation of the FAST TRACK unit is discussed in detail in U.S. Pat. No. 4,924,107, the disclosure of which is hereby incorporated by reference.

Each camera employed by this invention preferably comprises a high sensitivity, high resolution, solid state, MOS (metal oxide semiconductor) television camera with a sensitivity of at least 5 Lux. Such a camera is capable of capturing the images of the respective interior portions of the container, all while the container is moving along a conveyor line. A camera suitable for use with this invention is available from Panasonic Corporation, Model GP-MF702/ Industrial MOS B/W camera, equipped with a 50 mm lens.

This invention may be integrated into a container manufacturing line to allow 100 percent inspection of containers. In such an operation, additional apparatus may be employed in combination with this invention. Such additional apparatus may include part-present detectors to detect the presence of a container at the inspection stations and deliver an appropriate signal to initiate the inspection sequences, and/ or to detect the presence of a container at the rejection station and deliver an appropriate signal to initiate a rejection sequence. Should the invention detect an unacceptable defect or flaw as determined by the vision computer, the invention may generate an appropriate rejection signal directed to a remote rejection machine to initiate the removal of the unacceptable container from the manufacturing line.

A method provided by this invention for inspecting the interior surface portions of objects such as metal beverage container 10 through the open top thereof generally comprises illuminating at least the upper interior portion 15, forming a first image of one interior portion of the container 10 generally above the container 10 using an annular ellipsoidal reflector, capturing the first image thus formed by an image-sensing means, forming a second image of another interior portion of the container generally above the container using a planar image-splitting mirror, capturing the second image thus formed by a second image-reproducing means, combining the first and second images to thereby form a resultant composite image of substantially the entire upper portion surface of the container, and capturing a third image of a lower interior surface portion by a third image-reproducing means at a separate location. The method of this invention can additionally include the step of analyzing the captured images for defects.

This invention more particularly includes a method for acquiring an image of substantially the entire interior surface of an open top metal beverage container such as container 10 having an upper portion 11 forming the open top and a lower portion 12 forming a closed end. The image-acquiring method preferably comprises the steps of: illuminating the interior of said container from above the open top thereof with an illuminator 25; providing a first image-sensing means, such as a television camera 42, arranged with its central optical axis generally coincidental with a central axis 10a of the container, thereby defining a first light path therebetween; providing a second image-sensing means, such as a second camera 62, positioned outside of the first light path with its central optical axis disposed at an angle to the central axis 10a of the container along a second light path; providing an annular, ellipsoidal first reflector 30 arranged above the container along the first light path; providing a planar second reflector 50 arranged above the container along the first light path; reflecting light from the circumferential interior surface 15 of the upper portion 11 of the container generally along the first light path; forming a first image corresponding to the circumferential interior surface 15 of the container with the first reflector 30; capturing the first image thus formed with the first image sensing means 40; reflecting light from the flange 14 of the upper portion 11 of the container generally along the second light path; forming a second image corresponding to the flange 14 of the container with the second reflector 50; capturing the second image thus formed by the second reflector 50 with the second image-sensing means 60 located along the second light path; analyzing the first and second images with an image-processing means 70; providing a third image-sensing means 140 at a separate location arranged with its central optical axis generally coincidental with the central axis of the container, thereby defining a third light path therebetween; reflecting light from a lower interior portion 12 of the container toward the third image-sensing means 140; and capturing the third image with the third image-sensing means 140. The preferred method of this invention further includes the steps of analyzing the images thus captured by the cameras for defects.

In a further embodiment, this method includes the steps of: providing a fourth image-sensing means 160 at the separate location outside of the third light path with its central optical axis disposed at an angle to the central axis 10a of the container along a fourth light path; providing a planar image-splitting third reflector 150 at the separate location between the container and the third image-sensing means 140 along the third light path; reflecting light from the bottomwall 18 of the container with the third reflector 150; deflecting the light reflected from the bottomwall 18 of the container along the fourth light path toward the fourth image-sensing means 160 with the third reflector 150, whereby a corresponding fourth image is formed; and capturing the fourth image thus formed by the third reflector 150 with the fourth image-sensing means 160.

The method of this invention preferably additionally includes the steps of combining the first and second images and the third and fourth images to generate first and second resultant composite images 100 and 101, respectively, and determining whether defects exist in either image. Such a method can be used advantageously for the inspection of metal beverage containers during or after their manufacture.

As illustrated in FIG. 4A, the forming of first image 102 corresponding to upper interior portion 15 is carried out by annular reflector 32, which has interior reflecting face 34 that forms an enlarged image of upper interior portion 15. Image 102 is preferably then captured by camera 42. The forming of second image 104 corresponding to the flange 14 of the container is carried out by planar reflector 52 (FIG. 4B) and second image 104 is then captured by second camera 62. The capturing of the third image 106 is carried out preferably at a second location station by third camera 142 viewing the lower interior portion 12 directly and capturing its image accordingly. The forming of the fourth image corresponding to the bottomwall 18 of container 10 is carried out by planar reflector 152 arranged at the second inspection station and the fourth image 108 is then captured by fourth camera 162.

The illuminating step of this method is carried out by annular diode array 27 disposed generally above the container 10, and preferably above the annular reflector 32, to direct diffused light rays 29 generally downwardly and radially inwardly to illuminate at least the upper interior portion 15 of the container 10. Where the illuminating step of this invention creates an intense reflection from flange portion 14 that cannot be accommodated by the lens of one of the camera means, the method can include the step of filtering the high intensity light reflected from the flange portion 14, for example, by an annular filter 90 as indicated in dashed lines in FIG. 2.

While the present specification describes the system and method of this invention in reference to the inspection of metal beverage containers through an opening in the top thereof, this invention is not limited to such metal containers. This invention may be utilized for the inspection of the interior portion(s) of any opaque container or article that has reflective properties such that a defect in the container or article results in a variation in light reflection that may be detected optically.

This invention thus permits a machine vision inspection system to acquire images of substantially the entire interior surface of a typical metal beverage container at two inspection stations along a manufacturing line by employing a novel combination of television cameras, reflectors, an optical filter, and vision computers. The systems and method of this invention provide inspection systems for metal containers that perform more economically and with much better reliability and repeatability than prior known systems and methods.

Although the system and method provided by the present invention have been described with a preferred embodiment, those skilled in the art will understand that modifications and variations may be made without departing from the scope of this invention as set forth in the following claims. Such modifications and variations are considered to be within the purview and scope of the appended claims.

We claim:

1. In a system for inspecting the interior surface of an open top cylindrical opaque object, said object having a flange portion circumscribing said open top and a neck portion of decreased radius disposed below said flange, the improvement comprising:

a first system for inspecting an upper interior region of said object, said first system comprising:

means arranged above the open top of said object for illuminating the interior of said object in a front-lighting arrangement downwardly through the open top of said object;

a first means located above the open top of the object for forming a first image of the interior of said neck portion of the object, said first means comprising an annular reflecting member having an inwardly facing reflecting surface for forming an image of the interior of said neck portion;

a second means located above the open top of the object for capturing and reproducing said first image corresponding to said neck portion interior of the object from said image-forming first means;

a third means located above the open top of the object for forming a second image of the flange portion of the object;

a fourth means located above the open top of the object for capturing and reproducing said second image corresponding to said flange portion of the object;

a fifth means coupled to said image-reproducing second and fourth means for electronically masking and combining said first and second images to generate a single resultant composite image for defect analysis corresponding to the upper interior portion and flange portion of said object, and a second system for inspecting a lower interior portion of said object, said second system comprising:

a sixth means located above the open top of the object for capturing and reproducing a third image corresponding to said lower interior portion of said object.

2. The inspection system as in claim 1 further comprising means coupled to said image-producing sixth means of the second system for analyzing for defects said third image corresponding to the lower interior portion of said object.

3. The inspection system as in claim 1 wherein the fifth means of said first system is defined by a vision computer for analyzing for defects said resultant composite image.

4. The inspection system as in claim 1 wherein said illuminating means comprises an illuminator arranged above the open top of said object for irradiating the upper interior portion of said object with diffused light rays, said illuminator comprising an annular array of light-emitting diodes.

5. The inspection system of claim 1 wherein said second system further comprises:

an eighth means located above the top of the object for forming a fourth image of the bottom of the object;

a ninth means located above the open top of the object for capturing and reproducing said fourth image corresponding to said bottom of the object;

means coupled to said image-reproducing fifth and ninth means for electronically masking and combining said third and fourth images to generate a second resultant composite image for analysis corresponding to the lower interior portion of said object.

6. The inspection system as in claim 5 wherein said image-forming third and eighth means each comprise a planar reflecting member.

7. The inspection system as in claim 6 wherein each said planar reflecting member comprises a partially silvered image-splitting mirror, said image-splitting mirrors being adapted to lie generally on the central axis of said object and in a plane angularly disposed in relation to said central axis.

8. The inspection system as in claim 7 wherein each said image-splitting mirror is disposed at an angle of approximately 45 degrees in relation to the central axis of the object, and said image-reproducing fourth and ninth means are arranged with their central axes approximately 90 degrees in relation to the central axis of said image-reproducing second means and of said object.

9. The inspection system as in claim 5 wherein said image-reproducing second, fourth, fifth and ninth means each comprise a television camera.

10. The inspection system as in claim 5 wherein said object comprises a metal beverage container having an open top, a necked portion adjacent to the open top, a closed end defined by a bottomwall opposite the open top of the container, and a cylindrical sidewall extending between the necked portion and the bottomwall of the container, wherein the lower interior portion of the object comprises the cylindrical sidewall of the container generally below the necked portion, and wherein the bottom portion of the container includes a moat portion, a crown portion, and a chime portion.

11. The inspection system as in claim 1 wherein said annular reflecting member comprises an upwardly concave truncated ellipsoidal mirror arranged with its central axis coinciding with a central axis of said object.

12. The inspection system as in claim 1 wherein said image-forming first and third means and said illuminating means are positioned generally between the object to be inspected and said image-reproducing second means, and wherein said image-forming first means, said image-reproducing second means, and said illuminating means are arranged generally coaxially with each other and with a central axis of said object.

13. The inspection system as in claim 1 further comprising machine interface means for allowing the inspection system to communicate with a remote rejection machine; and operator interface means coupled to the inspection system for allowing an operator to communicate with the inspection system.

14. The inspection system as in claim 1 wherein said object comprises a metal beverage container having a necked portion, said top of the object comprises a flange of said container, and said upper interior portion comprises a circumferential interior surface area of the necked portion of said container, and wherein light rays are reflected from the flange and the upper interior portion of said container.

15. The inspection system as in claim 1 wherein the interior of the neck portion of said object has a three-dimensional topography, and said image-forming first means unfolds the three-dimensional image of said neck portion interior and generates a two-dimensional flat plan view thereof for defect analysis.

16. The inspection system as in claim 1 wherein said image-forming first means further directs light rays downwardly through the open top of said object to substantially uniformly illuminate the interior surface of said neck portion.

17. A system for inspecting substantially the entire interior surface of a metal container, said container having an open end, a closed end, an upper portion adjacent to the open end and a lower portion adjacent to the closed end, said upper portion including a flange circumscribing the open top of said container and a necked portion of decreased radius extending downwardly therefrom, said lower portion including a cylindrical sidewall and a bottomwall forming said closed end, said necked portion integrally connecting said cylindrical sidewall to said flange, said system comprising:

first and second image-sensing means located at a first inspection station generally above the container to be inspected;

a third image-sensing means located at a second inspection station generally above the container to be inspected;

an annular illuminator located generally above the container to be inspected at the first inspection station for irradiating at least the annular circumferential interior surface of the necked portion of said container;

a first reflecting member located at the first inspection station arranged between the container to be inspected and one of said first and second image-sensing means, said first reflecting member comprising an upwardly concave ellipsoidal mirror, said first image-sensing means, illuminator and first reflecting member being arranged with their central axes generally coinciding with one another and with a central axis of said container;

a second reflecting member located at the first inspection station angularly disposed between said first reflecting member and the first image-sensing means generally along the central axis of said container, said second reflecting member comprising a planar image-splitting mirror;

a first image-processing means located at the first inspection station coupled to said first and second image-sensing means, and a second image-processing means located at the second inspection station coupled to said third image-sensing means, said first reflecting member being adapted to direct light rays from said annular illuminator to and intercept light rays reflected from the circumferential interior surface of the necked portion of said container and form a corresponding first image in the operating field of said first image-sensing means, said first image-sensing means being adapted to capture said first image thus formed, said second reflecting member being adapted to intercept light rays reflected from the flange of the upper portion of said container and form a corresponding second image in the operating field of said second image-sensing means, said second image-sensing means being adapted to capture said second image thus formed, said first image-processing means being adapted to electronically combine the first image corresponding to the circumferential interior surface of the necked portion of the container with the second image corresponding to the flange of the upper portion of the container to thereby generate a resultant composite image of substantially the entire upper portion of said container, said first image-processing means further being adapted to inspect said resultant composite image of defects and to generate a rejection signal if defects are present, said third image-sensing means being adapted, once the container is positioned at the second inspection station, to view and capture directly a third image of the lower interior portion of the container, said second image-processing means being adapted to inspect said third image for defects and to generate a rejection signal if defects are present.

18. The inspection system as in claim 17 further comprising:

a fourth image-sensing means located at the second inspection station generally above the container to be inspected; and a third reflecting member located at the second inspection station angularly disposed between said third image-sensing means and the container to be inspected generally along the central axis of the container, said third reflecting member comprising a planar image-splitting mirror;

and wherein said third image-sensing means is arranged coaxially with the central axis of the container to be inspected, said fourth image-sensing means being disposed at a right angle with respect to the third image-sensing means, said third reflecting member being adapted to intercept light rays reflected from the bottomwall of said container and form a corresponding fourth image in the operating field of said forth image-sensing means, said fourth image-sensing means being adapted to capture said fourth image thus formed, said second image-processing means being adapted to electronically combine the third image corresponding to the lower interior portion of the container with the fourth image corresponding to the bottomwall of the container to thereby generate a second resultant composite image of substantially the entire interior surface of the container generally below the necked portion, said second image-processing means being further adapted to inspect said second resultant composite image for defects and to generate a rejection signal if defects are present.

19. The inspection system as in claim 17 wherein said pair of image-sensing means each comprises a television camera, and wherein said illuminator comprises an annular array of light-emitting diodes arranged generally above and radially outwardly from the open top of said container, said annular array being adapted to direct light rays generally downwardly and radially inwardly through the open top of said container to illuminate at least the circumferential interior surface of the necked portion of said container.

20. The inspection system as in claim 17 wherein said inspection system further comprises:

operator interface means for allowing an operator to communicate with the inspection system; and machine interface means for allowing the inspection system to communicate with a remote rejection machine.

21. The inspection system as in claim 17 wherein said resultant composite image of substantially the entire upper portion of said container comprises an inverted image having the image portion corresponding to the flange of the container disposed centrally of the resultant composite image and the image portion corresponding to the circumferential interior of the neck portion disposed radially outwardly of said flange image portion.

22. A dual-station system for inspecting the interior surface of an open top opaque metal beverage container, comprising:

a metal beverage container having an upper portion and a lower portion, said upper portion including a flange circumscribing said open top and a necked area having a reduced radius adjacent and below said open top, said lower portion including a cylindrical sidewall about its central axis and a bottomwall defining a closed end of said container;

conveyor means for transporting said container to the first station and therefrom to the second station;

an annular diffused light source located generally above the open top of the container, said light source being adapted to direct light onto the interior surfaces of the container from about the periphery of the open top of said container;

a first camera located at the first station generally above the open top of the container with its central optical axis coinciding with a central axis of said container;

an ellipsoidal annular first mirror located at the first station between the open top of the container and the first camera and generally surrounding the open top of said container, said first mirror being adapted to direct light rays downwardly through the open top of said container to illuminate the interior of the necked area of said container and to intercept light rays reflected upwardly therefrom and form a first image of the interior portion of the necked area of the upper portion of said container within the field of vision of said first camera, said first camera being adapted to view and capture said first image;

a second camera located at the first station generally above said container with its central optical axis disposed angularly to the central axis of said container and to the central optical axis of said first camera;

a planar image-splitting second mirror located at the first station angularly disposed along the central axis of the container between the container and the first camera, said second mirror being adapted to form a second image of the flange of the upper portion of said container within the field of vision of said second camera, said second camera being adapted to view and capture said second image;

a first vision computer coupled to said first and second cameras thereafter for receiving first and second images for electronically masking and combining said first and second images, whereby a resultant composite image of substantially the entire upper portion of the container is formed, and for analyzing the resultant composite image for defects, a third camera located at a second station generally above the open top of the container with its central optical axis coinciding with the central axis of said container, said third camera being adapted to view and capture a third image corresponding to the sidewall of the lower portion of said container;

a fourth camera located at the second station with its central optic axis disposed angularly to the central axis of said container and to the central optical axis of said third camera;

a planar image-splitting third mirror located at the second station angularly disposed along the central axis of the container between the container and the third camera, said third mirror being adapted to form a fourth image of the bottomwall of said container within the field of vision of said fourth camera, said fourth camera being adapted to view and capture said fourth image; and a second vision computer coupled to said third and fourth cameras receiving said third and fourth images for electronically masking and combining said third and fourth images, whereby a second resultant composite image of substantially the entire lower portion of the container is formed, and for analyzing the second resultant composite image for defects.

23. A method of acquiring images of interior surface portions of an opaque container having a lower end, an open upper end, and a neck portion of decreased radius adjacent the upper end of the container, said method comprising the steps of:

directing light downwardly through the open upper end onto the interior surface portions of the container;

forming and capturing a first image of a first interior surface portion adjacent the open upper end of the container;

forming and capturing a second image of a second interior surface portion adjacent the open upper end of said container;

electronically combining said first and second images to form a resultant image of substantially the entire upper portion of said opaque container; and capturing a third image of an interior surface portion adjacent to the lower end of said container.

24. The image-acquiring method as in claim 23 wherein the step of forming the first image is carried out by reflecting light from said first surface portion adjacent the open upper end of the container with an ellipsoidal reflecting member, said ellipsoidal reflecting member being disposed generally above the container and being adapted to form said first image of said first surface portion from the light rays reflected therefrom.

25. The image-acquiring method as in claim 23 wherein the step of forming the second image is carried out by reflecting light from said second interior surface portion adjacent to the lower end of the container with a planar image-splitting reflecting member, said planar image-splitting reflecting member being disposed generally above the container and being adapted to form said second image of the second interior surface portion from the light rays reflected therefrom.

26. The image-acquiring method as in claim 23 wherein said light source is defined by an illuminator comprising an annular array of light-emitting diodes arranged generally above and around said container for radiating light rays generally downwardly and radially inwardly at the interior of the open upper end of said container.

27. The image-acquiring method of claim 26 wherein the open upper end of said container includes a highly reflective planar surface circumscribing said open end which is illuminated by said light source, and wherein said image-acquiring method further comprises the step of filtering the light rays reflected from said highly reflective planar surface.

28. The image-acquiring method as in claim 23 wherein the first image is captured with an image-sensing means arranged generally above the container with its central optical axis coinciding with a central axis of the container.

29. The image-acquiring method as in claim 23 wherein the step of forming and capturing said first image comprises the steps of:
providing a first camera located above the open upper end of the container;
providing an ellipsoidal mirror located between the container and the first camera and generally surrounding the open upper end of the container;
forming the first image of a circumferential interior surface portion adjacent the open upper end of the container generally above the container with said annular mirror within the field of view of the first camera; and
capturing said first image with the first camera via the annular mirror,
wherein said step of forming and capturing said second image comprises the steps of:
providing a second camera located generally above the container and at an angle to said first camera;
providing a planar mirror located between the container and the first camera;
forming said second image of a flange of said container generally above the container with said planar mirror within the field of view of the second camera; and
capturing said second image with the second camera via the planar mirror,
and wherein said step of capturing said third image comprises the steps of:
providing a third camera located at a separate station generally above the open upper end of the containers; and
viewing the lower interior surface portion of said container and capturing the third image corresponding thereto.

30. The image-acquiring method as in claim 23 further comprising the step of substantially uniformly illuminating the interior of the neck portion of said container by directing light rays downwardly through the open upper end of the container with an ellipsoidal reflecting member.

31. A method of acquiring images of interior surface portions of an opaque container having an open upper end and a lower end, said method comprising the steps of:
directing light onto said interior surface portions of the container;
forming and capturing a first image of a first interior surface portion adjacent the open upper end of the container;
forming and capturing a second image of a different second surface portion adjacent the open upper end of said container; and
combining said first and second images to form a resultant image of substantially the entire upper portion of said opaque container.

32. A system for inspecting an interior surface area of an open top, cylindrical, non-transparent object, comprising:
means arranged above the open top of said object for illuminating the interior of said object downwardly through the open top of said object in a front-lighting arrangement;
means located above the open top of the object for forming a first image of a first portion of said interior area of the object, said image-forming means comprising an annular reflecting member having an inwardly facing reflecting surface for forming an image of the first portion of said interior area;
means located above the open top of the object for capturing and reproducing said first image corresponding to the first portion of said interior area of the object;
means located above the open top of the object for forming a second image of a second portion of said interior area of the object;
means located above the open top of the object for capturing and reproducing said second image corresponding to the second portion of said interior area of the object; and
means coupled to said image-reproducing means for electronically combining said first and second images for generating a single resultant composite image corresponding to substantially the entire interior area of the object for defect analysis.

33. A method of acquiring an image of an interior surface area of an opaque object having a lower end and an open upper end, said method comprising the steps of:
directing light downwardly through the open upper end onto the interior surface of the object;
forming and capturing a first image of a first portion of the interior surface area;
forming and capturing a second image of a separate second portion of the interior surface area; and
electronically combining said first and second images to form a single resultant composite image of substantially the entire interior surface area of opaque object.

* * * * *